United States Patent
Yang et al.

(10) Patent No.: US 11,435,301 B2
(45) Date of Patent: Sep. 6, 2022

(54) REACTION CONTROL AND MASS SPECTROMETRY WORKSTATION FOR COUPLING AN X-RAY SPECTROSCOPIC CHARACTERIZATION INSTRUMENT WITH AN IN-SITU REACTION CELL

(71) Applicant: SHANGHAITECH UNIVERSITY, Shanghai (CN)

(72) Inventors: Yong Yang, Shanghai (CN); Zebang Liu, Shanghai (CN); Jerry Pui Ho Li, Shanghai (CN); Evgeny Vovk, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 531 days.

(21) Appl. No.: 16/613,801

(22) PCT Filed: May 25, 2018

(86) PCT No.: PCT/CN2018/084392
§ 371 (c)(1),
(2) Date: Nov. 15, 2019

(87) PCT Pub. No.: WO2018/210108
PCT Pub. Date: Nov. 22, 2018

(65) Prior Publication Data
US 2020/0173939 A1    Jun. 4, 2020

(30) Foreign Application Priority Data
May 17, 2017    (CN) .......................... 201710347554.2

(51) Int. Cl.
*G01N 23/207*    (2018.01)
*H01J 49/04*    (2006.01)
*H01J 49/24*    (2006.01)

(52) U.S. Cl.
CPC ...... *G01N 23/2076* (2013.01); *H01J 49/0422* (2013.01); *H01J 49/24* (2013.01)

(58) Field of Classification Search
CPC .... G01N 23/2076; G01N 23/22; G01N 27/62; G01N 27/622; H01J 49/0422; H01J 49/24
See application file for complete search history.

(56) References Cited

FOREIGN PATENT DOCUMENTS

| CN | 105510264 A | 4/2016 |
| CN | 105702554 A | 6/2016 |

(Continued)

OTHER PUBLICATIONS

Kehres et al., "Novel Micro-Reactor Flow Cell for Investigation of Model Catalysts Using In-Situ Grazing-Incidence X-Ray Scattering", Journal of Synchrotron Radiation, 2016, 23, 455-463 (Year: 2016).*

(Continued)

*Primary Examiner* — David E Smith
(74) *Attorney, Agent, or Firm* — Bayramoglu Law Offices LLC

(57) ABSTRACT

A reaction control and mass spectrometry workstation for coupling an X-ray spectroscopic characterization instrument with an in-situ reaction cell, including a reactant gas composition control module and an online gas composition analyzing module. The workstation further involves a modification based on the original vacuum pipeline section. After the modification, the original vacuum pipeline section is connected to three customized gas ports, and the modification is characterized in that the vacuum manifold unit is additionally provided with a mass spectrometer sampling port, a sampling capillary, and control valves. The present disclosure has the following advantages. The sampling time delay can be ignored in the mass spectrometry, and the sampling is continuous real-time in-situ analysis with high (Continued)

time resolution. Under the working conditions of the X-ray spectroscopic characterization instrument, the electronic structure/crystal structure information and the precise information of the ambient gas composition are obtained simultaneously.

6 Claims, 2 Drawing Sheets

(56) References Cited

FOREIGN PATENT DOCUMENTS

| | | |
|---|---|---|
| CN | 106449348 A | 2/2017 |
| CN | 107238618 A | 10/2017 |

OTHER PUBLICATIONS

Jan Kehres et al. Novel Micro-reactor Flow Cell for Investigation of Model Catalysts Using in Situ Grazing-incidence X-ray Scattering. Journal of Synchrotron Radiation. Mar. 31, 2016. vol. 23, pp. 455-463.

* cited by examiner

REACTION CONTROL AND MASS SPECTROMETRY WORKSTATION FOR COUPLING AN X-RAY SPECTROSCOPIC CHARACTERIZATION INSTRUMENT WITH AN IN-SITU REACTION CELL

CROSS REFERENCE TO THE RELATED APPLICATIONS

This application is the national phase entry of International Application No. PCT/CN2018/084392, filed on Apr. 25, 2018, which is based upon and claims priority to Chinese Patent Application No. 201710347554.2, filed on May 17, 2017, the entire contents of which are incorporated herein by reference.

TECHNICAL FIELD

The present invention belongs to the field of basic chemical reaction kinetics research of online reaction control, component detection and kinetics characterization, and the present invention is especially focused on: the coupling characterization of an X-ray spectroscopy method and a mass spectrometer for a reaction process, while crystal or electronic structure of a research object is precisely observed, expanding the function so as the components of reaction gas in its environment is simultaneously and continuously recorded in real time, so as to establish interrelation between these two characterizations. The present disclosure is also applicable to real-time continuous detection of gas components in other similar radioactive environments.

BACKGROUND

X-ray spectroscopy equipment is special in measurement condition, namely a radioactive environment. According to the structure defined for observation, characterization of the basic properties of a measuring object such as the crystal structure, the electronic structure, etc., are provided respectively, such as an X-ray diffraction device (XRD), small-angle X-ray scattering (SXAS) and X-ray absorption spectra (XAS, XANES, EXAFS). However, because X-ray is in use as a detection light source, the working area of the X-ray has radioactivity harmful to the human body, and must be isolated from persons by a lead plate or radiation protective glass and the like, which causes great limitation to the extension of the experiment scope. An X-ray in-situ reaction cell is an accessory for introducing chemical reaction to the X-ray spectroscopy equipment, so as to realize X-ray spectroscopy measurement in the reaction environment. In such characterization process, the variety of reaction environments may affect the property of the measuring object, and reflect in the measurement result of an X-ray spectrogram, so as to establish a direct causal relationship between the reaction environment and the change of related properties of the measuring object in transient-state or steady-state measurement, which leads to a further insight into important chemical reaction, it is an important means for understanding and improving representative chemical reaction (involving, for example, a denox process, a methane oxidative coupling process and the like). In such types of measurements, the precise quantification of the reaction environment components and the related time resolved change are of great importance.

The influence induced by the limitation from the radioactive environment must be taken into consideration for the reaction environment components control and measurement undergoing with the X-ray instrument characterization work. Obviously, any control or measurement methods from a third party must not change the original safety protection setup of the X-ray spectroscopic characterization instrument, and the customized installation may only be performed outside an equipment safety housing. By analyzing from components control, the components of a reactant entering the in-situ reaction cell may be precisely controlled by gas or liquid flow ratio, namely an incoming gas mixing device outside the equipment, but the gas components is also bound to the change along with the actual reaction progress. For example, if the characteristics of a catalyst in a carbon monoxide oxidization process are observed, the reaction components before input is a precisely mixed gas of carbon monoxide and oxygen, but carbon dioxide will be produced in the in-situ reaction cell. If a carbonate crystalline phase is generated in the bulk phase of the measuring object, the corresponding in-situ data of the new components of the carbon dioxide gas is thus extremely important for discussion and conclusion. Therefore, continuous real-time online components analysis must be performed on the in-situ reaction cell in the X-ray spectroscopic characterization instrument if a causal relationship needs be truly established between the reaction environment and the properties of the measurement object.

Therefore, the main problem of the foregoing components analysis is ascribed as following: performing gas components analyzation within the in-situ reaction cell inside the equipment, while strictly abiding the prerequisite of not changing and not entering the interior of the X-ray spectroscopic characterization instrument. Besides, it should be noted that the air pressure range of an in-situ reaction cell disposed for the X-ray device is generally between 0.1 MPa and 1 MPa, which is of the range from ambient pressure to medium high pressure. This also exceeds the upper limit of a sampling pressure of the general commercially available gas components analyzing devices, such as a gas chromatograph (GC) and a mass spectrometer (MS).

Currently, the third-party manufacturers design the in-situ reaction cells for quite a few of X-ray spectroscopy characterization instruments, but there are no matched reaction gas components control scheme and online gas components analysis in general.

SUMMARY

The technical problem to be solved by the present invention is: performing gas components analyzation within the in-situ reaction cell inside the instrument, while strictly abiding the prerequisite of not changing and not entering the interior of the X-ray spectroscopic characterization instrument.

In order to solve the foregoing technical scheme, the technical scheme of the present invention provides a reaction control and mass spectrometry workstation for coupling an X-ray spectroscopic characterization instrument with an in-situ reaction cell. The reaction control and mass spectrometry workstation includes a reactant gas composition control module and an online gas composition analyzing module. The present disclosure further involves a modification based on the original vacuum pipeline section. After the modification, the original vacuum pipeline section is connected to the analyzing workstation via a combined exhaust gas output port, an in-situ reaction cell exhaust gas output port and an in-situ reaction cell mixture gas input port, and the modification is characterized in that the vacuum manifold unit is additionally provided with a mass spectrometer sampling port, a sampling capillary, and control valves, wherein:

the online gas composition analyzing module obtains a trace gas sample from the in-situ reaction cell exhaust gas output port through a capillary via the mass spectrometer sampling port; the online gas composition analyzing module includes a mass spectrometer electric quadrupole, a molecular pump set, and a needle valve/high precision metering valve; an originally configured mechanical pump for an in-situ reaction cell and a molecular pump set draw sampled gas out from the capillary through a corresponding pumping gasline, respectively; part of the gas drawn out from the capillary tube flows toward the mass spectrometer electric quadrupole, and the other part flows into the originally configured mechanical pump, and the flow ratio between the gas to the mass spectrometer electric quadrupole and to the originally configured mechanical pump is modulated by the needle valve/high precision metering valve;

the reactant gases composition control module comprises a mixture gas supply manifold, a single gas supply manifold, a gas manifold switching unit, and a pressure regulating unit; wherein the two gas manifold supplies, namely, from the mixture gas supply manifold and the single gas supply manifold, are switchable by the gas passage switching unit, so that one of the two gas manifolds is connected to the in-situ reaction cell mixture gas input port, and the other one of the two gas passages joins together with the in-situ reaction cell exhaust gas output port and then is connected to the combined exhaust gas output port; pressures at the gas manifold terminal connected to the in-situ reaction cell mixture gas input inlet and the gas manifold terminal connected to the combined exhaust gas output port are each regulated by a corresponding pressure regulating unit.

Preferably, the gasline connected to the in-situ reaction cell exhaust gas output port has a relatively small inner diameter, so that the total interior volume of the manifold between the in-situ reaction cell exhaust gas output port and the capillary tube is much smaller than the dead volume of the in-situ reaction cell.

Preferably, the capillary is an inlet diameter reduced metal capillary tube.

Preferably, the online gas composition analyzing module and the reactant gas composition control module are respectively arranged on an upper layer and a lower layer of a two-layer tool cart; and the online gas composition analyzing module is connected to the mass spectrometer sampling port through one of the four vacuum ferrule fitting connection ports or quick connection ports on one panel board; the reactant gas composition control module is connected to the other three vacuum ferrule fitting connection ports or quick connection ports on the same panel board, the combined exhaust gas output port, the in-situ reaction cell exhaust gas output port, and the in-situ reaction cell mixture gas input port.

Preferably, two ends of the capillary are connected to the originally configured mechanical pump and the mass spectrometer sampling port through a corresponding controlling ball valve set, respectively.

Preferably, the mixture gas supply manifold includes three mass flow controllers respectively connected to three kinds of gases, and the three kinds of gas outputs from the three mass flow controllers are mixed together to form a gas mixture with compositions ratio defined by up to three precise flowrates; and the pure gas supply manifold includes a mass flow controller, and a flow of the pure gas is precisely controlled by the mass flow controller.

The present invention solves the following technical problems.

Technical problem I: not changing the radiation protection structure of the original instrument. The X-ray spectroscopic characterization instrument has radioactivity in a test environment, and therefore, the complete machine has a complete radiation protection structure for the safety of the user. The foregoing structure must be kept complete when new test functions are added, and should not have any change. Taking into comprehensively consideration of the instrument requirement limitation and the technical characteristics of the collection of the gas components analysis signal, the connection between the mass spectrometer and the instrument may be compatible with this limitation. In the process that the in-situ reaction cell is both in the working state and characterized by the X-ray, although in a radioactive environment, the reaction gas does not carry radioactivity in consequence. The in-situ reaction cell itself also has pipelines connected with a gas input and an output ports outside the instrument, so as to ensure the normal operation of the reaction in the in-situ cell. Therefore, the mass spectrometer should be sampling from an exhaust pipeline connecting to the in-situ reaction cell outside the instrument, thus is may analyze the gas components in the reaction cell by without changing the radiation protection structure of the X-ray spectroscopic characterization instrument.

A certain spatial distance is bound to exist between the exhaust duct outside the X-ray spectroscopic characterization instrument and the in-situ reaction cell, and by adopting such solution, it must consider the retardation of mass spectrum signal collection. Generally, none of the in-situ reaction cell of the X-ray instrument is a micro reaction cell, and an internal dead volume generally reaches 100 mL or above. Therefore, for pipeline connection of the in-situ reaction cell, the supplier is required to adopt a pipeline with a relatively small diameter to reduce the volume increase caused by the pipeline as much as possible. If a 3 mm metal pipeline is used with the inner diameter of about 1.5 mm, and the total connection length of about 1.5 mm, and it is calculated that the total volume in the pipeline is 1.5 m*nt*(1.5 mm)²/4, about 2 mL, which is by far smaller than the dead volume of the in-situ reaction cell itself, and the generated time delay is negligible.

Technical problem II: enabling the ambient pressure of the sampling part to conform to the parameter scope of the in-situ reaction cell of the X-ray spectroscopic characterization instrument. The in-situ reaction cell of the X-ray spectroscopic characterization instrument, for example, XRK900, reaches the upper limit air pressure of 1 MPa in working, which belongs to a middle-high pressure scope. Generally, commercial mass spectrometers require that the air pressure in a sampling area is one atmospheric pressure, namely, 0.1 MPa. Even if it is defined that mass spectrometry is only performed in the in-situ reaction cell at the air pressure of about 0.1 MPa, because the capillary and the mass spectrometer are directly connected together, due to the influence of the overall volume, certain space limitation will exist in the connection of the commercial mass spectrometer with the exhaust port of the in-situ reaction cell, and it needs to further extend the length of the exhaust pipeline outside the instrument to facilitate the connection. In this way, the foregoing time delay may be further increased. Moreover, relatively long glass fiber capillary is generally used for the commercial mass spectrometer, and the chromatographic effect will also cause certain time delay. Therefore, the commercial mass spectrometer has defects in both time delay and air pressure adaptability.

According to the present invention, a comprehensive scheme of a mass spectrometer electric quadrupole and a input diameter reduced metal capillary as well as an independent differential pump disclosed by the invention patent application (hereinafter referred to as prior patent) with application number of 201610140435.5 provided by the applicant before is adopted, which is applicable to an air pressure scope of 0.1 to 2 MPa. Meanwhile, because the metal capillary is compatible with universal ferrule installation, a pipeline with a relatively large inner diameter, for example, a stainless steel pipeline with size of ¼ inch or greater, is suitable for connection between the capillary and the mass spectrometer. This part of the pipeline is in a vacuum state during the test work of the mass spectrometer and will not cause time delay. In this way, the metal capillary with very small diameter and volume is directly connected to the sampling port at the position where the exhaust duct of the in-situ reaction cell is at the shortest distance from the outside of the instrument, so as to minimize the time delay. Therefore, compared with current commercial instrument, the present invention has the both flexibility and accuracy measurement advantages in time delay and the air pressure range of the sampling area, the two of which are measurement indexes closely related to the in-situ reaction cell of the X-ray spectroscopic characterization instrument.

Technical problem III: realizing a small volume, and quick dismounting and removal of the in-situ reaction cell when not in working. Currently, the third-party manufacturers design the in-situ reaction cells for quite a few of X-ray spectroscopy characterization instruments, but there are no matched reaction gas components control scheme and online gas components analysis basically. If the laboratory establishes the foregoing scheme according to the common design of chemistry and chemical engineering, the control instrument and the mass spectrometer will occupy a very large fixed space, and the user interface of the original instrument is not clear, and therefore, dismounting and mounting and connection are inconvenient, thus limits other functions of the X-ray spectroscopy instrument, making the instrument become a special platform of the accessory of the in-situ reaction cell. The in-situ XRD and in-situ XAS in some laboratories have no online mass spectrometer and only used for low-conversion/non-conversion reaction or complete conversion reaction which are easy in components deduction while sacrificing partial conversion reaction which is with more general applicability; or because the installation of the in-situ reaction cell extension function is relatively complicated, and the dismounting is difficult, thus only used as instrument with a single function in actual operation, and therefore, other functions of the X-ray instrument are sacrificed finally.

Aiming at the problem, the present invention provides a solution easy in dismounting, including providing mixed gas input with accurate components control, gas switching with certain degree of freedom, air pressure control range from 0.1 to 1.0 MPa, and mass spectrum gas components analysis with accuracy to ppm or higher level. The gas input control part includes 4 to 6 mass flow controllers, divided into two paths of gas, one four-way switching valve, two sets of back pressure regulators and a pressure sensor; the mass spectrum components analysis part includes a mass spectrometer electric quadrupole and a matched molecule pumping set. Moreover, a set of complete computer equipment is also included to provide necessary equipment monitoring program and data record. All equipment is installed on a small-size double-layer plastic tool cart with a bottom plate area of 70*50 cm, and connected with the X-ray spectroscopic characterization instrument by four ferrule connections or quick connections on one panel. After use is stopped, the upstream gas is cut off, and only several minutes are needed to dismount the connectors and push away all additional devices, so that the exterior of the X-ray spectroscopic characterization instrument restores to the original installation state.

Generally, X-ray characterization methods are limited to the shell structure of electron and the crystal phase bulk structure, and are insensitive to isotopic components and the like, and therefore, an upstream gas mixing device has already met the basic requirement of the X-ray spectroscopic characterization instrument by switching between three paths of mixed gas and one path of pure gas. The space of such design may accommodate switching of two groups of three paths of mixed gas at most to be used for upstream gas supply.

As previously mentioned, tail gas produced by the in-situ reaction cell of the X-ray spectroscopic characterization instrument does not carry radioactivity under ray irradiation, and therefore, special radiation protection treatment does not need to be performed on the sampling pipeline and the analysis instrument as well as tail gas after analysis. Selection of material of the gas pipeline of the instrument is consistent to the material of the pipeline originally installed by the manufacturers. That is, a metal stainless steel or red copper clean pipeline with ferrule connections.

Technical problem IV: sharing and utilizing existing hardware of the original equipment. The in-situ reaction cell of the X-ray instrument is generally provided with an originally configured mechanical pump (vacuum limit is $10^{-2}$ torr) for performing pre-vacuum-pumping on the reaction cell, so as to ensure that the reaction gas is not affected by residual gas in the reactor, and achieves an experiment predetermined ratio rapidly. When the in-situ reaction cell works, gas is input according to experiment requirements, and the mechanical pump is stopped and idle. In the prior patent adopted by the present invention, an independent differential pump set needs to be used to adjust the mass spectrometer to achieve a steady injection volume under different sampling ambient pressures. Moreover, the highest air pressure scope needed in the present invention is lower than the air pressure scope of the prior patent, and the requirement for the highest pumping speed and vacuum degree of the independent differential pump set is not strict. Therefore, the mechanical pump conforms to the requirement of the independent differential pump, and is in an idle state all the time when the in-situ reaction cell works. In present invention, when in-situ gas mass spectrometry is needed, the mechanical pump is adopted as the independent differential pump necessary for the sampling scheme of the prior patent, and thus not only increasing the utilization rate of the mechanical pump, but also saving space of the control and sampling equipment, and further optimizing the pipeline design needed for gas sampling.

To sum up, the present invention has the following special design.

1. On the basis of a mass spectrum gas components sampling analysis scheme of the prior patent, aiming at special requirements of the instrument in the present invention, the distance between the capillary and the X-ray spectroscopic characterization instrument is shortened to the greatest extent by optimizing vacuum connection.

2. Modular design is used, that is, many constituent parts of the present invention are divided into two major modules, including mass spectrometer/gas pipeline control instrument and sampling port/differential pump set, which are connected by simple gas pipeline ports. Meanwhile, no original setting of the X-ray spectroscopic characterization instrument is changed.

3. On the basis of the mass spectrum gas components sampling analysis scheme of the prior patent, highly integrated installation and simplest treatment of a connecting interface between the modules are achieved, including: 1) two paths of switchable mixed gas sources formed by 4 to 6 mass flow controllers and one four-way switching valve; 2) gas pressure control equipment formed by two sets of back pressure valves and a pressure sensor; 3) a mass spectrum gas components analysis instrument including the mass spectrometer electric quadrupole and the matched molecule pumping set; and 4) one set of computer providing complete equipment monitoring program and data record for the equipment. All of the above are installed on a small-size double-layer plastic tool cart with a bottom plate area of 70*50 cm, and connected with the X-ray spectroscopic characterization instrument by four ferrule connections or quick connectors in a same panel.

4. The hardware of the original instrument is sufficiently utilized, and one differential pump is shared with the mass spectrum gas components sampling analysis scheme of the prior patent.

Based on the foregoing special design, the present invention has the following advantages.

1. In mass spectrum gas sampling components analysis, sampling time delay may be neglected, and the sampling analysis requirements of in-situ analysis as continuous and real-time and high time resolution are achieved.

2. In the working conditions of the X-ray spectroscopic characterization instrument, while the electronic structure/crystal structure is obtained, precise information of the components of the environment gas is simultaneously obtained, instrument functions are extended, and in-situ multi-dimensional characterization is realized.

3. An experimental purpose upstream gas source necessary for operation, which is steady, and precisely controlled in components and pressure, and with rapid switching function, is provided for the in-situ reaction cell.

4. It is safe and does not have the radiation safety problem.

5. Auxiliary instrument is easy in mounting and dismounting, without affecting implementation of any function of the original instrument.

6. Cost is saved, and space utilization is minimized.

7. Sampling analysis meets the pressure condition of the in-situ reaction cell of the X-ray spectroscopic characterization instrument.

DETAILED DESCRIPTION OF THE EMBODIMENTS

To make the present invention more comprehensible, preferred embodiments are described in detail below with reference to the accompanying drawings.

Figure 1:
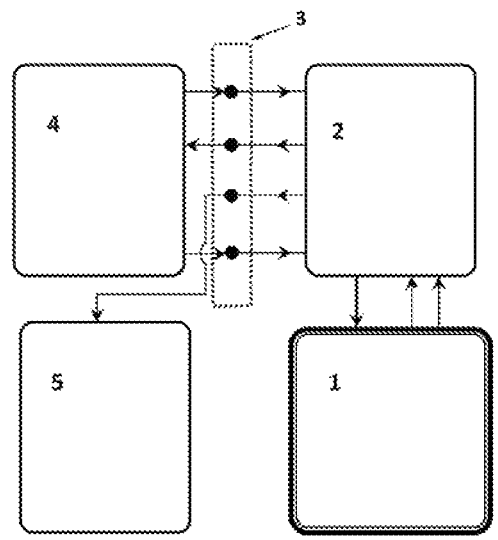
FIG. 1 is a layout schematic diagram of a mass spectrometer and X-ray spectroscopic characterization instrument.

The basic design layout of the scheme of the present invention is as shown in FIG. 1, an X-ray characterization equipment cabinet 1 is connected with a vacuum pipeline section 2 of the in-situ reaction cell according to the original design. In the original instrument, only the vacuum pipeline section 2 of the in-situ reaction cell is slightly altered for sampling of the mass spectrometer, while the radiation protection design of the X-ray characterization equipment cabinet 1 is not modified in any form. The original instrument region is connected with an upper layer 4 (a reactor gas mixture switching and gas pressure control panel, an operation interface monitor) of the reaction control and mass spectrometer workstation for coupling an in-situ cell with X-ray spectroscopic characterization instrument and a lower layer 5 (a mass spectrometer, a computer controller section) of reaction control and mass spectrometer workstation for coupling an in-situ cell with X-ray spectroscopic characterization instrument by the XRD and gas pipeline centralized connection ports 3 (totally four). The whole reaction control and mass spectrometer workstation for coupling an in-situ cell with X-ray spectroscopic characterization instrument is integrated on a small-size double-layer plastic tool cart with a bottom plate area of 70*50 cm.

Figures 2A, 2B:
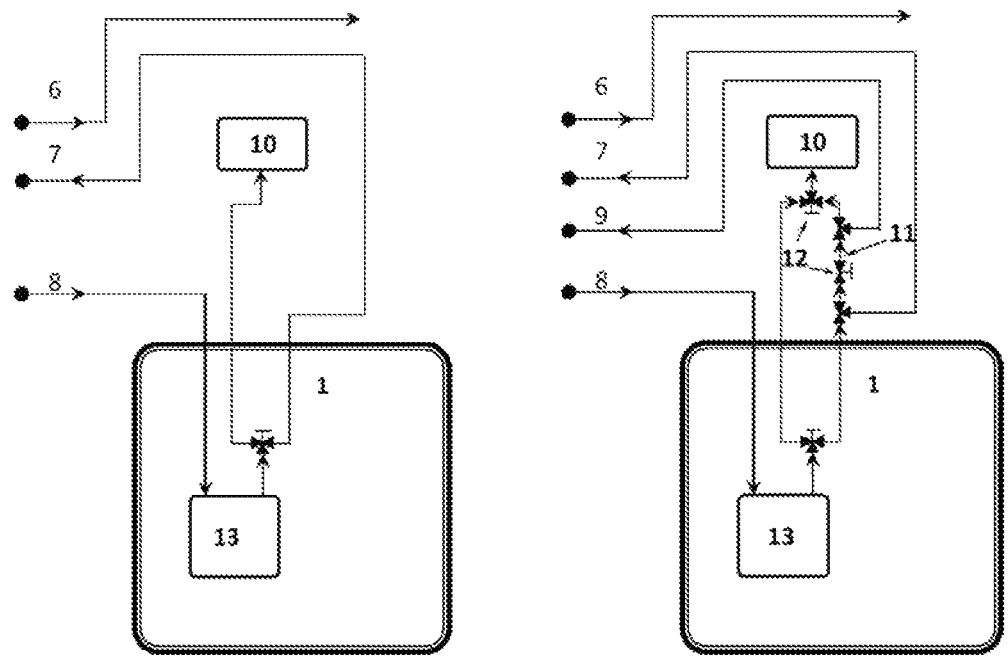
FIG. 2A is an original gas pipeline outside the X-ray spectroscopic characterization instrument.
FIG. 2B is a schematic diagram after the original gas pipeline outside the X-ray spectroscopic characterization instrument is changed according to the present invention.

FIG. 2A is a connection schematic diagram of the vacuum pipeline section of the in-situ reaction cell without modification, the X-ray characterization equipment cabinet 1 is connected with an external gas pipeline by three pipeline connections, namely, the combined exhaust gas output port 6, the in-situ reaction cell exhaust gas output port 7 and the in-situ reaction cell mixture gas input port 8. An originally configured mechanical pump 10 is connected to the in-situ reaction cell 13 by switching a three-way valve in the original design of the manufacturer, so as to provide for-evacuum needed by the in-situ reaction cell 13 before starting to work. After the in-situ reaction cell 13 starts to react and measure, the three-way valve is switched to the in-situ reaction cell exhaust gas output port 7 to evacuate reaction gas. As shown in FIG. 2B, aiming at the connection relation shown in FIG. 2A, a fourth pipeline connector, namely, a mass spectrometer sampling port 9, is added to be matched with the gas components sampling analysis function of the instrument of the present invention. The fourth pipeline is a branch for performing gas microsampling on the in-situ reaction cell exhaust gas output port 7 via the capillary 11. The capillary 11 is at zero distance from the X-ray characterization equipment cabinet 1, so as to reduce the pipeline distance from the in-situ reaction cell 13, and then time delay generated therefrom is negligible. On the branch of the mass spectrometer sampling port 9, the capillary 11 connects with the in-situ reaction cell exhaust gas output port 7 and the originally configured mechanical pump 10 at the same time by changing a control ball valves set 12, so as to provide continuous and real-time trace gas sampling to the mass spectrometer sampling port 9.

Figure 3:
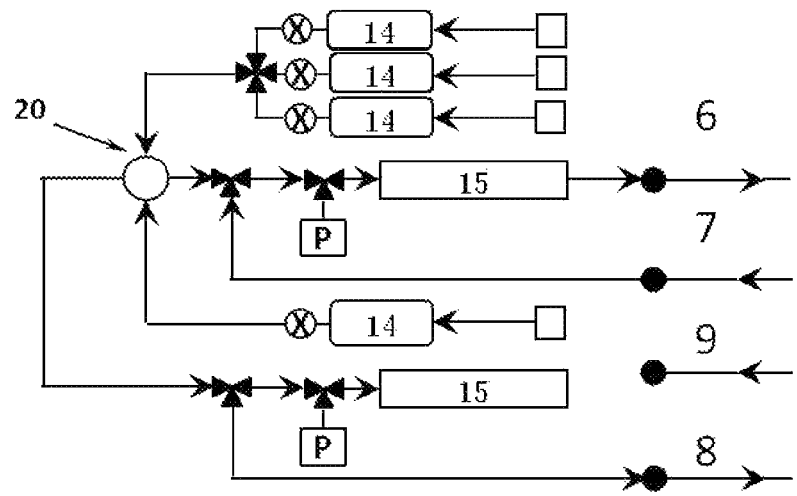
FIG. 3 is an upper-layer layout of a reaction control and gas components characterization workstation of an in-situ cell of the X-ray instrument in the present scheme.

The reaction control and mass spectrometer workstation for coupling an in-situ cell with X-ray spectroscopic characterization instrument is integrated on a small-size double-layer plastic tool cart with a bottom plate area of 70*50 cm, which is the core part of the instrument. FIG. 3 is the upper layer 4 part (a computer display is not shown) of the station, namely, a control panel providing the upstream gas flow rate and mixed components as well as downstream terminal pressure of the in-situ reaction cell 13, which is a stainless steel panel of 50*50 cm. Incoming gas is divided into two paths of gas. One path is mixed gas, the mixed gas with precise ratio of three flow rates and component at most being formed by three mass flow controllers 14, the other path is single gas, of which the flow rate is precisely controlled by one mass flow controller 14. The two paths of gas are switched by a four-way valve 20, one path is connected with the in-situ reaction cell mixture gas input port 8, and the other path selects to converge with the in-situ reaction cell exhaust gas output port 7 and then leads to the combined exhaust gas output port 6. Terminals of the two paths of gas both maintain pressure by back pressure regulators 15, so as to achieve the set in-situ reaction cell experimental gas components and gas pressure requirements. Combining with the original temperature control of the in-situ reaction cell, multiple steady-state and transient-state chemical processes are realized, such as, steady-state reaction, isothermal adsorption/desorption, temperature-programmed desorption/oxidization/reduction (TPD/TPO/TPR). While the crystal structure/electronic structure of the observed object in different temperature, pressure and environment components is obtained by the X-ray spectroscopic characterization instrument, the corresponding reaction activity and the characteristic changes of various reaction energy barriers are obtained simultaneously.

Figure 4:
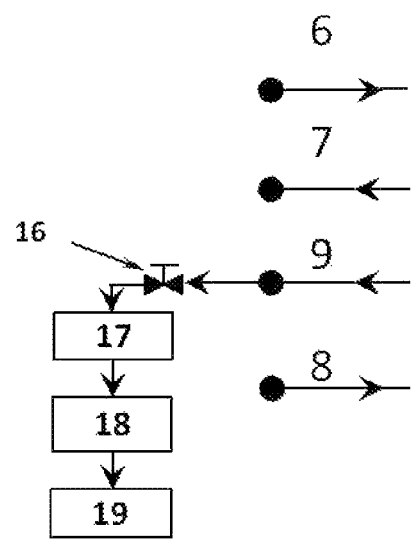
FIG. 4 is a lower-layer layout of a reaction control and gas components characterization workstation of an in-situ cell of the X-ray instrument in the present scheme.

FIG. 4 is the lower layer 5 part (a computer mainframe is not shown) of the workstation, namely, the mass spectrometer electric quadrupole 17 and the molecule pumping set for providing mass spectrum gas components analysis, the molecule pumping set includes a turbo molecular pump 18 and a primary pump 19. The front end of the mass spectrometer electric quadrupole 17 is connected with the mass spectrometer sampling port 9 by a needle valve/high-precise metering valve 16 and a ¼ inch stainless steel vacuum pipeline. The combination of FIG. 4 and FIG. 2B jointly realizes the structure of the mass spectrum gas components sampling analysis scheme of the prior patent, and the design structure is optimized correspondingly according to special requirements of the present invention while achieving the design parameters of the prior patent.

The present invention is further described in combination with concrete data hereinafter.

According to the present invention, in implementation in a laboratory, an imported SRS200 electric quadrupole matched with a Pfeiffer HiCube80 turbo molecular pumping set of KF connection, is used as a mass spectrometer platform for testing the device of the present invention, and when being sealed, the background air pressure is $5*10^{-8}$ torr. The used X-ray spectroscopic characterization instrument is an X-ray diffractometer (BrukerD8), the matched in-situ reaction cell is XRK900, the air pressure scope is 0.1 to 1.0 MPa, the air temperature scope is from room temperature to 900 Celsius degree, and the originally configured mechanical pump is Edward brand. Other domestic made equipment includes that the used mass flow controller is the series of Sevenstar CS200A precise flowmeter, and the upper limits of flow rates are respectively 10, 20, 50 sccm (mixed gas) and 200 sccm (single gas). The main valve (the upstream leads to the in-situ reaction cell mixture gas input port 8) of the back pressure regulator is Xiongchuan 250 psi, and the auxiliary valve (the upstream converges with the downstream of the in-situ reaction cell exhaust gas output port 7 to lead to the combined exhaust gas output port 6) is X-Tec250 Psi. The computer is a domestic industrial control unit, IPC-610L, which provides the installation of control and data collection software for the mass spectrometer electric quadrupole, and the pressure sensor, as well as the mass flow controller. The mass spectrometer software is original, and other software is programmed by force control (Likong) software.

In installation, the distance from the capillary to the X-ray spectroscopic characterization instrument is shortened as much as possible, to reduce the gas delay time in the pipeline, and this delayed time in relative to the dead volume of the in-situ reaction cell is negligible. The capillary 11 is connected to the pipelines of the mass spectrometer sampling port 9 and the originally configured mechanical pump 10 and then is directly adapted with a stainless steel pipeline of an amplified outer diameter of ¼ inch or more, so as to realize maximal vacuum conductance. That is, the connection with the mass spectrometer instrument achieves zero time delay.

The combined exhaust gas output port 6, the in-situ reaction cell exhaust gas output port 7, the in-situ reaction cell mixture gas input port 8 and the control ball valve set 12 in FIG. 2B are all installed on a same operation panel close to the X-ray characterization equipment cabinet 1, so as to facilitate dismounting and experimental operation.

By the modular installation design, various constituent parts of the present invention are divided into two major modules, including mass spectrometer/gas pipeline control equipment and sampling port/differential pump set, and meanwhile, the radiation protection structure is reserved completely and the safety use requirement is met while functions are added without altering any original setting of the X-ray spectroscopic characterization instrument.

On the basis of the mass spectrum gas components sampling analysis scheme of the prior patent, highly integrated installation and simplest treatment of a connecting interface between the modules are achieved, including: 1) two paths of switchable mixed gas sources formed by 4 to 6 mass flow controllers and one four-way switching valve; 2) gas pressure control equipment formed by two sets of back pressure valves and a pressure sensor; 3) a mass spectrum gas components analysis instrument including the mass spectrometer electric quadrupole and the matched molecule pumping set; and 4) one set of computer providing complete equipment monitoring program and data record for the equipment. All of the above are installed on a small-size double-layer plastic tool cart with a bottom plate area of 70*50 cm, and connected with the X-ray spectroscopic characterization instrument by four ferrule connections or quick connections in a same panel. Mounting and dismounting of connection with the X-ray spectroscopic characterization instrument are completed in several minutes. That is, it is restored to the original unmodified state from the characterization instrument state in which the in-situ reaction cell is accessed, or restored to the characterization instrument state in which the in-situ reaction cell is accessed from the original unmodified state.

Hardware of the original instrument is sufficiently utilized, a differential pump is shared with the mass spectrum gas components sampling analysis scheme of the prior patent, and use space and instrument cost are saved.

To sum up, according to the present invention, complete gas supply, pressure control and real-time in-situ gas components mass spectrum sampling analysis instrument are provided for the in-situ reaction cell of the X-ray spectroscopic characterization instrument, and the analysis function is extended. The gas supply and pressure control sections meet gas pressure and gas components accuracy requirements of the in-situ reaction cell of the X-ray spectroscopic characterization instrument; and the sampling part meets 1) the real-time sampling requirement, no time delay, and sensitive in response to the collection of trace pulses; 2) the air pressure range of the in-situ reaction cell of the X-ray spectroscopic characterization instrument, namely, the upper limit requirement of middle-high pressure, and 3) the safety requirement of the X-ray spectroscopic characterization instrument. Meanwhile, the installation is simple and convenient, the volume is small, the modules are clear, use of other functions of the original instrument and activities of workers are not affected. The present invention also plays a role of assisting in monitoring or fundamental research in chemical engineering reaction in other similar related environments.

What is claimed is:

1. A reaction control and mass spectrometry workstation for coupling an X-ray spectroscopic characterization instrument with an in-situ reaction cell, comprising: a vacuum pipeline section, a reactant gas composition controlling module and an online gas composition analyzing module; wherein the vacuum pipeline section comprises a combined exhaust gas output port, an in-situ reaction cell exhaust gas output port, an in-situ reaction cell mixture gas input port and a mass spectrometer sampling port; wherein, the online gas composition analyzing module obtains a trace gas sample from the in-situ reaction cell exhaust gas output port through a capillary via the mass spectrometer sampling port; the online gas composition analyzing module comprises a mass spectrometer electric quadrupole, a molecular pump set, and a needle valve/high precision metering valve; an originally configured mechanical pump for an in-situ reaction cell and a molecular pump set draw sampled gas out from the capillary through a corresponding pumping gasline, respectively; a first part of the gas drawn out from the capillary tube flows toward the mass spectrometer electric quadrupole, and a second part of the gas drawn out from the capillary tube flows into the originally configured mechanical pump, and a flow ratio between the first part of the gas to the mass spectrometer electric quadrupole and the second part of the gas to the originally configured mechanical pump is modulated by the needle valve/high precision metering valve the reactant gases composition control module comprises a mixture gas supply manifold, a single gas supply manifold, a gas manifold switching unit, and a pressure regulating unit; wherein two gas manifold supplies, namely, from the mixture gas supply manifold and the single gas supply manifold, are switchable by the gas passage switching unit, so that a first one of the two gas manifolds is connected to the in-situ reaction cell mixture gas input port, and a second one of the two gas passages joins together with the in-situ reaction cell exhaust gas output port and then is connected to the combined exhaust gas output port; pressures at the gas manifold terminal connected to the in-situ reaction cell mixture gas input inlet and the gas manifold terminal connected to the combined exhaust gas output port are each regulated by a corresponding pressure regulating unit.

2. The reaction control and mass spectrometry workstation for coupling an X-ray spectroscopic characterization instrument with an in-situ reaction cell according to claim 1, wherein, the gasline connected to the in-situ reaction cell exhaust gas output port has an inner diameter, so that a total interior volume of the manifold between the in-situ reaction cell exhaust gas output port and the capillary tube is smaller than a dead volume of the in-situ reaction cell.

3. The reaction control and mass spectrometry workstation for coupling an X-ray spectroscopic characterization instrument with an in-situ reaction cell according to claim 1, wherein, the capillary is an inlet diameter reduced metal capillary tube.

4. The reaction control and mass spectrometry workstation for coupling an X-ray spectroscopic characterization instrument with an in-situ reaction cell according to claim 1, wherein, the online gas composition analyzing module and the reactant gas composition control module are respectively arranged on an upper layer ayer tool cart and a lower layer of the two-layer tool cart; and the online gas composition analyzing module is connected to the mass spectrometer sampling port through one of the four vacuum ferrule fitting connection ports or quick connection ports on one panel board; the reactant gas composition control module is connected to the other three vacuum ferrule fitting connection ports or quick connection ports on the same panel board, the combined exhaust gas output port, the in-situ reaction cell exhaust gas output port, and the in-situ reaction cell mixture gas input port.

5. The reaction control and mass spectrometry station for coupling an X-ray spectroscopic characterization instrument with an in-situ reaction cell according to claim 1, wherein, two ends of the capillary are connected to the originally configured mechanical pump and the mass spectrometer sampling port through a corresponding controlling ball valve set, respectively.

6. The reaction control and mass spectrometry station for coupling an X-ray spectroscopic characterization instrument with an in-situ reaction cell according to claim 1, wherein, the mixture gas supply manifold comprises three mass flow controllers respectively connected to three kinds of gases, and the three kinds of gas outputs from the three mass flow controllers are mixed together to form a gas mixture with a compositions ratio defined by up to three precise flowrates; and a pure gas supply manifold comprises a mass flow controller, and a flow of a pure gas is precisely controlled by the mass flow controller.

* * * * *

UNITED STATES PATENT AND TRADEMARK OFFICE
CERTIFICATE OF CORRECTION

| | | |
|---|---|---|
| PATENT NO. | : 11,435,301 B2 | Page 1 of 1 |
| APPLICATION NO. | : 16/613801 | |
| DATED | : September 6, 2022 | |
| INVENTOR(S) | : Yong Yang et al. | |

It is certified that error appears in the above-identified patent and that said Letters Patent is hereby corrected as shown below:

On the Title Page

(22) PCT Filed Date should be:
--April 25, 2018--

Signed and Sealed this
Twenty-seventh Day of December, 2022

Katherine Kelly Vidal
*Director of the United States Patent and Trademark Office*